(12) United States Patent
Mallochet et al.

(10) Patent No.: US 9,050,380 B2
(45) Date of Patent: Jun. 9, 2015

(54) DEVICE FOR STORING AND RELEASING A FRAGRANCE, AND SET OF SUCH DEVICES

(75) Inventors: Cédric Mallochet, Bezons (FR); Christopher Sheldrake, Neuilly-sur-Seine (FR); Gaelle Madiot, La Garenne Colombes (FR)

(73) Assignee: CHANEL PARFUMS BEAUTE, Neuilly-sur-Seine (FR)

( * ) Notice: Subject to any disclaimer, the term of this patent is extended or adjusted under 35 U.S.C. 154(b) by 344 days.

(21) Appl. No.: 12/739,694

(22) PCT Filed: Oct. 24, 2008

(86) PCT No.: PCT/FR2008/001501
§ 371 (c)(1),
(2), (4) Date: Jul. 16, 2010

(87) PCT Pub. No.: WO2009/092874
PCT Pub. Date: Jul. 30, 2009

(65) Prior Publication Data
US 2011/0031327 A1    Feb. 10, 2011

(30) Foreign Application Priority Data
Oct. 25, 2007 (FR) ..................... 07 58572

(51) Int. Cl.
*A61L 9/12* (2006.01)
*A45D 34/02* (2006.01)
(Continued)

(52) U.S. Cl.
CPC .................. *A61L 9/127* (2013.01); *A45D 34/02* (2013.01); *A45D 34/04* (2013.01); *A45D 40/0087* (2013.01); *A45D 2200/058* (2013.01); *A45D 2200/1018* (2013.01); *A45D 2200/1036* (2013.01)

(58) Field of Classification Search
CPC ........... A61L 9/12; A61L 9/125; A61L 9/127; A45D 34/02; A45D 34/04; A45D 40/0087; A45D 2200/1018; A45D 1/1036; A01M 1/2044; A01M 31/008
USPC ............. 239/6, 34, 35, 44, 45, 47, 53–56, 71, 239/73, 326; 206/581
See application file for complete search history.

(56) References Cited

U.S. PATENT DOCUMENTS 1,129,897 A * 3/1915 Owen, Jr. .................... 239/45
4,847,124 A * 7/1989 Lux nee Andrieux ....... 428/34.2
5,031,764 A * 7/1991 Meador et al. ................ 206/232
(Continued)

FOREIGN PATENT DOCUMENTS

CH         385 436 A  * 12/1964
EP       0 297 959 A1 *  1/1989
(Continued)

*Primary Examiner* — Darren W Gorman
(74) *Attorney, Agent, or Firm* — Greenblum & Bernstein, P.L.C.

(57) ABSTRACT

The device for presenting a given fragrance comprises a presenting rod (10) in a confining enclosure (20), this confining enclosure comprising a collar (21) and this presenting rod comprising a porous portion (11) loaded with this fragrance and designed to fit through this collar, and another portion forming a head (12) suitable for grasping and designed to close this collar in a rest configuration such that the porous portion is, inside this confining enclosure, in a region where the fragrance exists in the gaseous state only, the constituent materials of the presenting rod underneath the head and those of the confining enclosure having no smell of their own.

35 Claims, 2 Drawing Sheets

(51) Int. Cl.
*A45D 34/04* (2006.01)
*A45D 40/00* (2006.01)

(56) References Cited

U.S. PATENT DOCUMENTS

| | | | | |
|---|---|---|---|---|
| 5,909,845 A | * | 6/1999 | Greatbatch et al. | 239/44 |
| 6,241,161 B1 | * | 6/2001 | Corbett | 239/58 |
| 6,745,950 B1 | * | 6/2004 | Longo | 239/44 |
| 2002/0094225 A1 | * | 7/2002 | Gueret | 401/183 |
| 2005/0220664 A1 | * | 10/2005 | Hitzler et al. | 422/5 |
| 2006/0071092 A1 | * | 4/2006 | Harris, Jr. | 239/44 |
| 2007/0140923 A1 | * | 6/2007 | Wiegand | 422/124 |
| 2008/0267832 A1 | * | 10/2008 | Chen | 422/123 |

FOREIGN PATENT DOCUMENTS

| | | |
|---|---|---|
| GB | 2389790 A | * 12/2003 |
| WO | WO 02083417 A1 | * 10/2002 |

* cited by examiner

DEVICE FOR STORING AND RELEASING A FRAGRANCE, AND SET OF SUCH DEVICES

CROSS-REFERENCE TO RELATED APPLICATIONS

This application is the U.S. National Phase of International Application Number PCT/FR2008/001501 filed on Oct. 24, 2008, which claims priority to French Application No. FR 0758572, filed Oct. 25, 2007, both of which are incorporated by reference herein in their entireties.

FIELD OF THE INVENTION

The invention relates to a device for storing and releasing a fragrance, particularly a perfume.

BACKGROUND

As is known, looking for fragrances, notably with a view to narrowing down a consumer choice, involves testing several fragrances in order ultimately to settle upon a given fragrance.

To do this, it is common practice to use strips of absorbent paper (in the field of perfumery, these are often referred to as "test strips"). More specifically, the demonstrator will present such strips in turn to her potential customer after having a sprayed onto them a small amount of one of the fragrances between which the choice is to be made.

However, such an approach has the disadvantage of entailing, for each fragrance, spraying an amount that often exceeds the amount that the strip of paper can absorb, thus leading to product losses (product vaporized beside the strip), to the risk of the formation of unsightly drips, to uncontrolled loading of each strip (some may be saturated while others are loaded with barely any perfume), making it difficult to compare the strength of the various fragrances, and also causing the environment to become progressively laden with all the fragrances tested, this gradually clouding one's perception of the new fragrances being proposed.

It should be noted that the fact that the strips are used just once means that the product remaining on the strip is thrown away when it has not yet completely evaporated.

Furthermore, use of simple strips of paper to present perfume, does not always allow the potential customer to be placed in the right frame of mind for evaluating the sophistication of the fragrances being proposed, especially in the case of luxury perfumes.

One special use of such strips has been proposed, which involves combining them with a bell-shaped dome placed on a flat surface and in the end of which the strip of paper is temporarily attached. This allows the strip of paper to release the fragrance with which it is loaded into the entire volume of the bell-shaped dome, thus allowing the potential customer to take a deep breath of the fragrance in order to assess the qualities thereof. However, such a solution takes up a significant amount of space on the flat surface in question, and does nothing to avoid mix-ups once a number of bell-shaped domes have been handled.

Another proposal has been to place impregnated cloths in enclosures which are successively opened up so that the cloths can be taken out and handled and the fragrances with which they are impregnated evaluated, but the disadvantage with that is that the demonstrator's fingers become saturated with the successive fragrances.

There is therefore a need to be able to present fragrances, such as perfumes, while minimizing product losses (which do nothing to assist with evaluating the product in question) and the risks of the surrounding atmosphere becoming inappropriately laden with perfume, while at the same time guaranteeing a certain consistency in how a given fragrance is presented and at the same time allowing the demonstrator to enact a certain amount of ceremony in demonstrating a plurality of fragrances; in practice, the aforementioned consistency corresponds to an objective to release the fragrance concerned in a pure and faithful manner, this entailing both storing the fragrance correctly and, at the opportune moment, reproducibly releasing this fragrance.

SUMMARY

The invention thus proposes a device for storing and releasing a given fragrance, comprising a presentation stick in a confining enclosure, this confining enclosure comprising a neck and this presentation stick comprising a porous portion laden with this fragrance and designed to pass through this neck and another portion forming a holding head designed to plug this neck in a rest configuration such that the porous portion is, inside this confining enclosure, in a zone in which the fragrance exists only in the gaseous state, the materials of which the presentation stick is made below the holding head and of which the confining enclosure is made having no odor of their own.

It will be appreciated that, according to the invention, the fragrance is thus stored, in its confining enclosure, mainly within the porous portion of the stick, and this minimizes the risks of product losses or drip formation; there is no longer any vaporization because the porous portion of the stick can be laden with fragrance simply by dipping it in liquid fragrance, outside of the confining enclosure, and therefore before the porous stick is engaged in its confining enclosure, and the fact that, when the stick is in its confining enclosure, this stick (or in any event, the porous portion thereof) is not in contact with fragrance in the liquid state, thus guaranteeing that there will be no drips formed. The fact that the stick has a head which plugs the neck of the confining enclosure minimizes the risk of the fragrance stored in this enclosure escaping to the outside, which means that the atmosphere will become very little (or even not at all) laden with this fragrance; further, because the fragrance stored in the confining enclosure cannot easily escape, it then follows that, when the stick is reengaged in this enclosure, the fragrance stored in the porous portion has only very little encouragement to evaporate in this enclosure, which means that this stick presents the fragrance under conditions that remain substantially identical over the course of the successive extractions from the confining enclosure.

It should be noted that, because the fragrance is stored mainly within the porous portion, transporting the presentation stick engaged in its confining enclosure allows the fragrance to be transported independently of any transportation of liquid, and this has the notable advantage of avoiding any risk of leakage.

The holding head is advantageously designed to prevent the fragrance from evaporating through this head. For this reason, this head is preferably made at least partially of a non-porous material; thus, for example, it is advantageously made of a non-porous material or, on the other hand, of a material that is porous (for example being of one piece with the stick) covered with a non-porous coating that prevents the fragrance from escaping.

Various additional features, potentially combined, are indicated below.

Thus, advantageously, this porous portion extends as far as a free end of the presentation stick, which makes it easier to load with fragrance, typically by dipping this porous portion into liquid fragrance and loading the porous mass under capillary action. Of course, the entirety of the stick, below the holding head, may be porous.

Advantageously also, the porous portion of the stick is, in the rest configuration, at a non-zero distance away from any potential liquid deposit of this fragrance inside the confining enclosure. It is therefore not excluded that there may be a liquid deposit of fragrance in the bottom of the confining enclosure, provided that this liquid deposit is not in contact with the porous portion of the stick; the presence of such a liquid deposit may have the advantage of guaranteeing that the internal volume of the confining enclosure is permanently saturated with fragrance, thus guaranteeing that the extent to which the porous portion is laden with this fragrance remains substantially constant over time.

Advantageously also, the confining enclosure is shaped and oriented in such a way that, in its rest configuration, the presentation stick is in contact with the confining enclosure only in the neck region, the presentation stick being suspended vertically from its holding head. That prevents the formation of a drip point at the contact between the stick and the inside of the confining enclosure.

Advantageously also, the confining enclosure comprises an internal wall which runs, at a clearance, along the external surface of the presentation stick under the holding head. That contributes to minimizing the volume of the confining enclosure and therefore the tendency that the fragrance has to evaporate outside of the porous portion when the stick is in the rest configuration.

Specifically, the fact that the confining enclosure more or less follows the contour of the porous part of the stick minimizes the risks of the release of fragrance into this enclosure when the stick is engaged therein; release of the fragrance therefore occurs under conditions that remain substantially constant each time this stick is extracted, whereas there is little (or no) risk of the atmosphere becoming laden with the fragrance stored in the gaseous state in the confining enclosure. Of course it must be understood that the idea of a clearance is to be interpreted in a broad sense and that, in practice, the distances involved may be several millimeters.

Advantageously also, the enclosure has an internal cross section the cross-sectional area of which is at least twice the cross-sectional area of the presentation stick, which guarantees that it will be easy to extract and engage the stick from and into the confining enclosure while at the same time minimizing the internal volume, and therefore the size, of the confining enclosure.

In practice, the cross section of the stick advantageously has dimensions ranging between 0.5 and 5 centimeters, and the internal cross section of the confining enclosure advantageously has dimensions ranging between 1 and 10 centimeters. Preferred ranges for these dimensions are from 1 to 3 centimeters in the case of the transverse dimensions of the internal cross section of the stick and from 1 to 5 centimeters in the case of the transverse dimensions of the internal cross section of the confining enclosure.

The sticks for example have a length ranging between 5 and 20 centimeters; the corresponding confining enclosure may have, in relation to the narrow part of the stick, a length that is greater by some arbitrary amount, for example ranging between 1 and 5 centimeters. In fact, the bottom of the confining enclosure may be bulged.

Advantageously, the cross section of the presentation stick and the cross section of the confining enclosure are, below the neck, substantially cylindrical; as an alternative, the cross section of the presentation stick and the cross section of the confining enclosure are, below the neck, substantially polygonal (for example square, rectangular, hexagonal, etc.). These cross sections may be more complex still so that, if desired, the stick can be engaged in its confining enclosure in just one angular configuration.

The porous part of the stick may be made from a wide variety of materials including wood, ceramics, etc.

For preference, devices of the aforementioned type are grouped together into a fragrance storage and release set (or fragrance presentation set for short) comprising a plurality of storing and releasing devices (or presentation sets) the confining enclosures of which are carried by one and the same support. These enclosures may be engaged immovably in holes in this support or, on the other hand, may be secured to this support, for example formed as an integral part thereof. The enclosures may be arranged in an array, for example in rows and columns or in a staggered configuration in particular.

For esthetic reasons, the presentation devices advantageously all have the same geometry within a given set. They may also have identical dimensions. As an alternative, the sticks and the confining enclosures of the various presentation devices rather have dimensions or geometries that are specific to themselves, guaranteeing that a stick cannot be engaged in some enclosure other than the one with which it is associated. That guarantees that there will be no contamination of one enclosure from a stick associated with another device.

Advantageously, the presentation set comprises stick-marking elements. These may be marks borne by the holding heads (for example recessed or raised or colored spots which are off-centered in relation to the holding head) that can be oriented in different ways according to the position of the stick in its enclosure, about its longitudinal direction. As an alternative, these marking elements are elements independent of the sticks and of the enclosures, such as rings able to raise a holding head in relation to the neck of the corresponding confining enclosure.

The invention also proposes a method for presenting fragrances (or for storing and releasing fragrances), comprising the following steps:

preparing a plurality of storing and releasing (or presentation) devices each comprising a presentation stick in a respective confining enclosure, this confining enclosure having a neck and this presentation stick having a porous portion able to pass through this neck and another portion forming a holding head designed to plug this neck in a rest configuration, that is, to close the opening at the upper end of the enclosure, such that the porous portion is inside this confining enclosure, the materials of which the presentation stick below the holding head is made and of which the confining enclosure is made having no odor of their own, loading each of the sticks with a particular fragrance and placing it in its rest configuration in its confining enclosure, the porous portion being in a region of the respective confining enclosure in which the fragrance exists only in the gaseous state, extracting a series of presentation sticks in succession and, according to the choices expressed by the demonstrator's correspondent, marking this stick as having been selected or not selected by fitting it back in its confining enclosure in the rest configuration, and once again, in succession, extracting at least some of the sticks marked as having been selected.

BRIEF DESCRIPTION OF THE DRAWINGS

Objects, features and advantages of the invention will become apparent from the description which follows, which is given by way of non-limiting illustrative example, with reference to the attached drawing in which.

DETAILED DESCRIPTION

Figure 1:
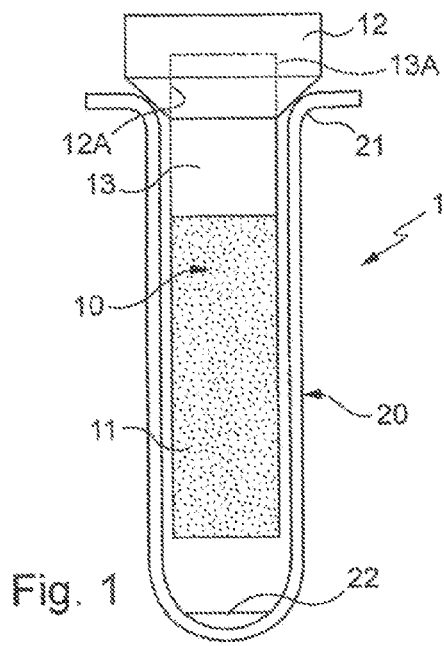
FIG. 1 is a view in vertical section of a presentation device according to the invention.

FIG. 1 depicts a device 1 for presenting a given fragrance, comprising a presentation stick 10 in a confining enclosure 20. This presentation device is able both to store and to release the fragrance in question.

The presentation stick 10 comprises a holding head 12 and a stick part, integrally formed with and depending from the holding head, the stick part having a porous portion 11 laden with fragrance.

The confining enclosure 20 has a neck 21 and the porous portion 11 of the presentation stick is designed to pass through the neck 21 while the other portion 12 is designed to plug the neck in a rest configuration, that is, to close the upper end of the confining enclosure 20, such that the porous portion is, inside the confining enclosure, in a region in which the fragrance exists only in the gaseous state. This rest configuration is depicted in FIG. 1 which also shows, in the bottom of the confining enclosure, a small liquid deposit 22, but this deposit is at a non-zero distance away from the porous portion and more generally from the presentation stick considered in its entirety. In fact, such a deposit is not sought after but may occur according to the conditions under which the porous portion of the presentation stick is loaded (that is to say impregnated) with fragrance.

In the example shown, the neck widens upward and, more specifically, the neck flares outwardly. In an alternative form that has not been depicted, it is simply formed, without the slightest chamfer, by the internal edge of the rim via which the enclosure can be held in a support (see FIG. 5). Likewise, the head may be simply formed by a portion of constant cross section greater than that of the stick, connected to this stick by a transverse angular shoulder.

For reasons concerned with the correct positioning of the holding head in relation to the neck, the presentation stick advantageously has a frustoconical portion where the head and the lower portion of the stick meet (this lower portion below the head is advantageously of a cross section which remains constant over its entire length, but could also have some other shape, for example could taper toward its free end).

The lower end of the stick proper here consists of a bottom face but, in an alternative form that has not been depicted, this end could be rounded (in other words, when this stick is of constant cross section, this constancy is no longer observed in the last few millimeters of this stick).

The materials of which the presentation stick is made (at least below the presentation head) and of which the confining enclosure is made, have no odor of their own, that is to say are neutral in relation to the fragrance and do not alter the perception thereof.

Mention may be made of the following materials:
neutral woods such as bamboo,
pumice stone,
porcelain,
rigid foams,
rigid sponges,
silica or calcium silicate (glass for example),
synthetic materials such as polymethylsiloxane,
vermiculite,
cellulose,
felts,
filters,
plastics, etc.

As an alternative, instead of being made of a rigid material, the porous portion may be made of a porous rigid envelope or may have a plurality of holes (made of a material such as those mentioned hereinabove) containing a soft material that can become laden with fragrance, a foam or a sponge for example. In any event, the porous portion of the presentation stick can be considered to be an absorbent portion, at least in the sense that is designed to hold or to become laden with the aforementioned fragrance, such as by means of pores or interstices.

For preference, the porous portion 11 extends down as far as a free end of the presentation stick, which is beneficial from the point of view of manufacture and also from the point of view of loading (impregnating) with fragrance. In addition, as shown, the porous portion 11 is fixed to or is integrally formed with the stick part of the presentation stick 10.

Specifically, the stick may be made of a single material, for the stick proper and for the lead thereof, and may even be made as one piece.

However, it is advantageous to make the presentation stick in two distinct parts; thus, FIG. 1 shows that the presentation stick 10 comprises a portion 13 of constant cross section and a portion that forms the holding head 12 and which comprises a housing 12A into which the upper end 13A of the portion 13 is fixed. This fixing may be achieved by any appropriate known means, notably using a screw thread, adhesive bonding or clip fastening. With the holding head 12 being fixed to the remainder of the presentation stick 10, that is, the stick part, by any of these means, it can be said that the holding head is integrally formed with the presentation stick.

When the presentation stick is made in several parts, these parts may be made of different materials, chosen according to the respective roles of these parts; thus, the material for the portion of constant cross section is chosen for its ability to become laden with fragrance in its porous part, while that of the holding head may be chosen according to esthetic criteria.

Of course, there may be more than two parts. Thus, the portion of constant cross section may be formed of two distinct parts one of which constitutes the porous portion chosen for its ability to become laden with fragrance and the other of which may have a more esthetic function. Likewise, the holding head may be formed of a core covered by a cap, for example made of precious metal (thus the head may be formed as one piece with the stick proper, and therefore of a porous material, possibly with a non-porous covering). If the part of constant cross section is attached removably, it may be replaced, keeping the head made of precious materials.

Various alternative forms of embodiment of the presentation stick are discussed hereinbelow with regard to FIGS. 9 to 12.

As for the confining enclosure, this may be made from a wide variety of materials given that its role is limited to that of containing, without altering it, the fragrance-laden stick. Thus it may, in particular, be made of glass, of metal (for example stainless steel) or of a synthetic material.

As is evident from FIG. 1, the confining enclosure 20 is advantageously configured and oriented in such a way that, in its rest configuration, the presentation stick 10 is in contact with the confining enclosure only in the neck region, the presentation stick being suspended vertically from its holding head. That way, there is no contact between the actual stick and the internal wall of the confining enclosure, and this reduces the risks of the formation of drips liable to detract from the presentation of the fragrance as the stick is extracted from the confining enclosure.

According to another advantageous feature of the invention, the confining enclosure 20 has an internal wall which, at a clearance, runs along the external surface of the presentation stick below the holding head (this clearance may be substantial, for example measuring several millimeters). That is why, in order to avoid there being a region of contact between the presentation stick and the confining enclosure below the neck, the enclosure is advantageously set vertically.

By way of an indication of the order of magnitude that the aforementioned clearance may represent, and which may potentially be substantial, it may be said that the enclosure has an internal cross section the cross-sectional area of which is at most equal to twice the cross-sectional area of the presentation stick, although in practice the clearance is at least equal to the order of a millimeter.

The lower part of the presentation stick (below the holding head) may be given various shapes, but it is advantageous, for reasons of manufacture and also of esthetics, for the chosen state to be uniform, that is to say to have an axis or some planes of symmetry. Thus, this lower part is advantageously of cylindrical section (and therefore has a circular cross section) that could also, as an alternative, be oval, or even have a number of dimensional maxima greater than three (for example the trefoil-shape).

As an alternative form that has not been depicted, this lower part may also have a cross section of polygonal, for example square, rectangular, triangular or hexagonal shape in particular.

This lower part may also have a more complex shape, so that it can be engaged in its confining enclosure only in one angular configuration.

Figure 2:
FIG. 2 is a view from above of the presentation stick of the device of FIG. 1, showing a first type of marking element.

In the example considered here, which is that of a stick of circular cross section, the confining enclosure has the overall shape of a cylindrical test tube. In this regard, as depicted in FIG. 2, for example, the confining enclosure is a cylindrical tube that is rounded at a lower end (i.e., a rounded longitudinal cross section), with a flared upper end at the neck 21, and a continuous uninterrupted inner surface from the lower end to the upper end.

The stick advantageously has a maximum transverse width of between 0.5 and 5 centimeters (preferably between 1 and 3 centimeters) while the internal cross section of the confining enclosure has a maximum transverse width of between 1 and 10 centimeters (preferably between 1 and 5 centimeters). The length of the stick (below the head) advantageously ranges between 5 and 20 centimeters and the enclosure may have its bottom situated between 1 and 5 cm away from the end of this stick.

The holding head may have a wide variety of shapes, namely basic shapes such as cylindrical shapes (such as in the example of FIGS. 1 and 2), oval or polygonal shapes, but may also have more fancy shapes such as may be found on the caps of perfume bottles (flower shapes, the shape of flames, of characters, etc.).

By way of example, the stick has a narrow part 10 mm in diameter, 120 mm long with a porous end portion 30 mm long, and a head 15 mm in diameter and 30 mm long (this stick is therefore 150 mm long). As for the enclosure, it is 124 mm tall (including a rim 3.9 mm tall) with an outside diameter of 14 mm (20 mm at the rim), a flat bottom and a thickness of 0.85 mm.

FIG. 2 depicts the holding head 12 of FIG. 1 viewed from above. It can be seen that there is a mark 12B away from the central region of this head, in this instance directed more or less along a radius of this head. This mark may be embodied by a groove, a rib, or an addition of color.

By way of an alternative that has not been depicted, when the head has an asymmetric shape, particularly in the case of a fancy shape (see above), the mark may simply consist of a detail (raised or recessed) of this fancy shape (for example a particular petal in the case of a flower pattern).

It will be understood that such a marking element allows the orientation of the presentation stick to be identified in relation to its confining enclosure. Indeed it is these marks borne by the holding heads that can be oriented in different ways according to the position of the stick in its enclosure (in order to be able to do this, all that is required is for the cross section of the neck to allow the presentation stick to be introduced in at least two possible configurations, for example in the case of an oval cross section; the foregoing is therefore not restricted to cases in which the lower part of the stick in cylindrical).

Figure 3:
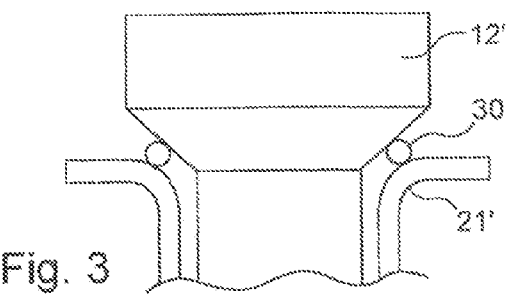
FIG. 3 is a view in section of the upper part of the device of FIG. 1 with another type of marking, independent of the stick and of the confining enclosure.
Figure 4:
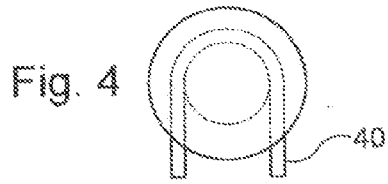
FIG. 4 is a view from above of the presentation stick of the same device with an alternative form of marking element.

FIGS. 3 and 4 show two other marking elements (that can be combined with the aforementioned marking) involving an accessory independent of the presentation stick and of its confining enclosure.

This accessory, labeled 30 in FIG. 3, is an annular ring that can be interposed between the neck 21' of the confining enclosure and the head 12' of the corresponding stick, which therefore finds itself raised up in relation to its normal position, that is, its normal rest position and, therefore, the raised-up position could be considered a second rest position, whereby neither the first nor the second rest position is a "presentation position," inasmuch as no porous portion of the presentation stick is yet withdrawn from the confining enclosure. A demonstrator can thus identify a fragrance, considered by a potential client to be of interest before making a later choice, by inserting a ring before returning the corresponding stick to its enclosure.

As an alternative, the marking element may be a U-piece, labeled 40 in FIG. 4, which can be used in the same way as the aforementioned ring, but which is easier to remove after the potential client has finalized his or her choice, without having to remove the stick from its enclosure completely.

Advantageously, a device for presenting a given fragrance (such as the one in FIG. 1 or a similar device) forms part of a set for storing and releasing fragrances (or, more simply, of a set for presenting fragrances) comprising a plurality of presentation devices the confining enclosures of which are borne by one and the same support.

Figure 5:
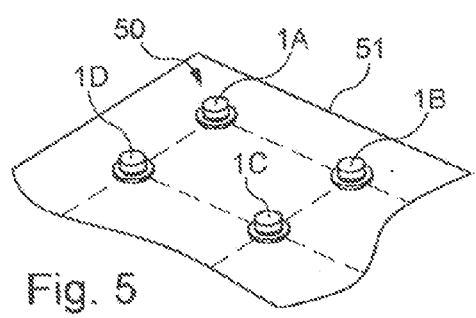
FIG. 5 is a partial perspective view of a collection of presentation devices like that of FIG. 1.

FIG. 5 thus shows an array, or collection, 50, of presentation devices labeled 1A, 1B, 1C, 1D here distributed in rows and columns on one and the same support labeled 51. By way of an alternative that has not been depicted, the devices are distributed in a staggered configuration. By contrast, the devices may be distributed unevenly, in a fancy pattern.

For preference, the devices in this array all have the same geometry. However, notably for esthetic reasons, provision may be made for the devices to be differentiated by row, or by column, or according to their position in relation to the periphery, etc. Provision may even be made for the sticks and enclosures of each presentation device to have specific dimensions or geometries to ensure that a stick can be engaged only in its own confining enclosure; in practice, it may be enough for the devices of this set in FIG. 5 to be differentiated from adjacent devices, so as to prevent a stick from being engaged in an enclosure close to the enclosure with which this stick belongs.

When demonstrating fragrances, the demonstrator thus has various fragrances available to her, under conditions that are very similar and the possible uniformity of the array of devices may contribute to the esthetic appeal of this demonstration.

Advantageously, marking elements, for example those described hereinabove, are provided so as to allow those fragrances from which the final selection will be made to be identified once each fragrance has been presented for a first time.

Figure 6:
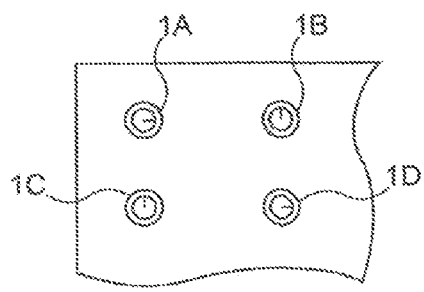
FIG. 6 is a view thereof from above, showing one possible use of the marking elements visible in FIG. 2.

FIG. 6 thus shows that the devices 1A and 1D have their marks oriented to the right while the devices 1B and 1C have their marks oriented upward. Depending on the conventions adopted by the demonstrator, this may mean that the fragrances contained in the devices 1B and 1C have been preselected for the next stage in the selection procedure, whereas the fragrances contained in the devices 1A and 1D have not been retained.

Figure 7:
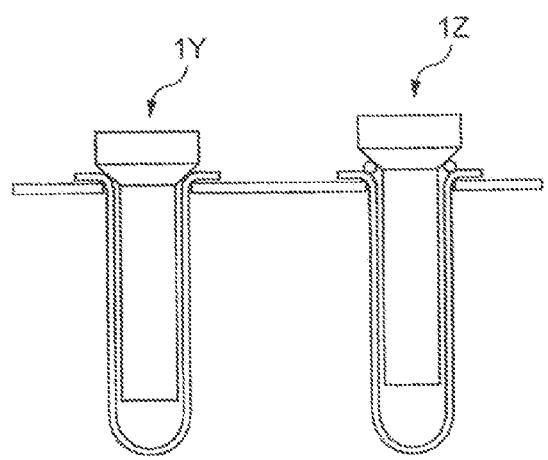
FIG. 7 is a partial view of the collection of FIG. 5 in cross section on a line connecting several devices, showing one possible use of the marking element of FIG. 3.

As for FIG. 7, it shows, side by side, two devices 1Y and 1Z, of which one (in this instance 1Z) has a ring interposed under its holding head. That may mean that the fragrance contained in the device 1Z has been retained for the next stage of the selection procedure, unlike the fragrance of device 1Y.

Of course, the demonstrator may adopt a wide variety of conventions, for example using rings of several colors (to characterize the comments made by the potential customer in particular) or to make several preselections (by interposing several rings under a head), etc.

An approach adopted when presenting fragrances typically involves the following steps:

preparing a plurality of presentation devices each comprising a presentation stick in a respective confining enclosure, this confining enclosure having a neck and this presentation stick having a porous portion able to pass through this neck and another portion forming a holding head designed to plug this neck in a rest configuration such that the porous portion is inside this confining enclosure, the materials of which the presentation stick below the holding head is made and of which the confining enclosure is made having no odor of their own, loading each of the sticks with a particular fragrance and placing it in its rest configuration in its confining enclosure, the porous portion being in a region of the respective confining enclosure in which the fragrance exists only in the gaseous state, extracting a series of presentation sticks in succession and, according to the choices expressed by the demonstrator's correspondent, marking this stick as having been selected or not selected by fitting it back in its confining enclosure in thereat configuration, and once again, in succession, extracting at least some of the sticks marked as having been selected.

Advantageously, a presentation device corresponds to a "neutral" fragrance, that is to say to a fragrance intended to restore the faculties of the person using it; thus, within the collection of presentation devices (which may also be termed a perfume organ), there might be a device the stick of which is impregnated with an extract of coffee or camphor, or impregnated with some other known non-floral odor so that the user can "clean" his or her sense of smell before continuing to evaluate the fragrances available to him or her; that will allow him or her to smell other fragrances and perceive the differences between them and the fragrances tested earlier.

FIGS. 8 to 14 show various alternative forms of embodiment of the presentation stick, of a device containing such a stick, or of a presentation set.

Figure 8:
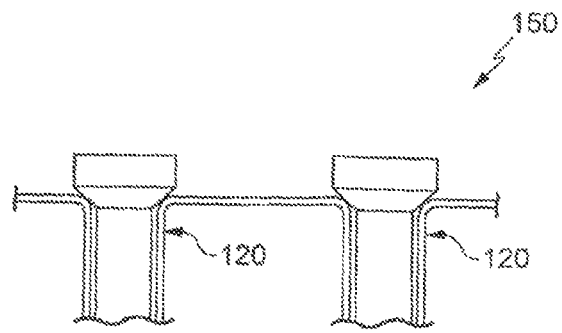
FIG. 8 is a view similar to that of FIG. 7, showing an alternative form of collection.

Thus, FIG. 8 shows an alternative form of embodiment of a fragrance presentation set 150 which differs from that of FIG. 7 in that the confining enclosures 120 which are borne by a common support, are no longer engaged in holes in this support such that in practice they can be removed therefrom, but are made of one piece with this support.

Moreover, various configurations may be proposed for creating a two-part presentation stick.

Figure 9:
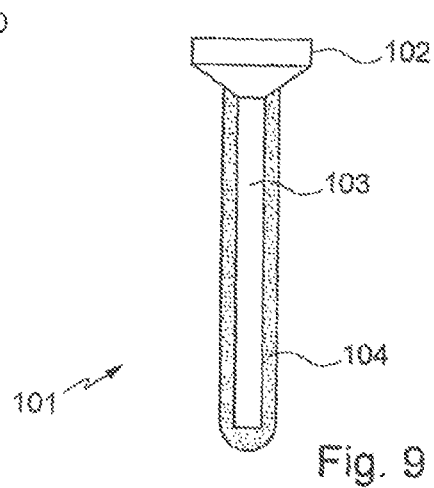
FIG. 9 is a view in cross section of an alternative for of the presentation stick.

The stick 101 in FIG. 9 thus comprises a head 102 secured to a central core 103, all made of appropriate material, metal for example, covered with a porous material 104; the central core thus constitutes a reinforcement capable of ensuring good rigidity independently of that of the porous material, while the latter can be chosen purely on the basis of its ability to be impregnated with the intended fragrances.

Figure 10:
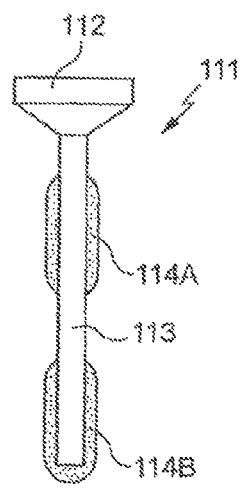
FIG. 10 is a view in cross section of another alternative form of the presentation stick.

FIG. 10 depicts an alternative thereof, labeled 111, whereby the porous material is affixed to the central core 113 over only part of the height thereof; in practice, this material is affixed at least to the lower part of this core, but there may also be one or more other portions at levels closer to the holding head. Here, there are two porous portions 114A and 114B (of smaller cross section than the head 112).

Figure 11:
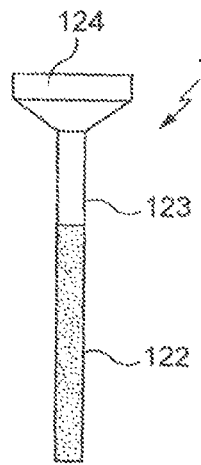
FIG. 11 is a view in cross section of yet another alternative form of the presentation stick.

FIG. 11 is an alternative form of FIG. 1, in which the stick 121 is made in two parts, namely a lower part 122 and an upper part 123; however, the interface between the upper and lower parts here lies somewhere between the bottom end of the stick and the holding head 124. The bottom part 122 advantageously corresponds to the porous portion 11 of FIG. 1.

Figure 12:
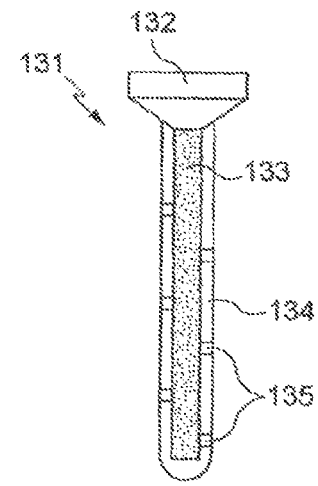
FIG. 12 is a view in cross section of yet another alternative form of the presentation stick.

In the reverse of that which is proposed in FIG. 9, the central part 133 of the stick 131 of FIG. 12 may be made of a porous material, that can be impregnated with fragrance, while this central part is surrounded by a sleeve 134 made of some other material, for example nonporous, here equipped with a plurality of ducts 135 providing communication between the porous central part and the outside. By way of example, this material of which the sleeve is made is enamel, which affords numerous esthetic effects.

Figure 13:
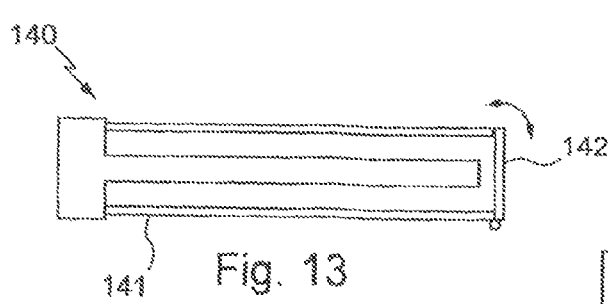
FIG. 13 is a view in cross section of an alternative form of a presentation device according to the invention.
Figure 14:
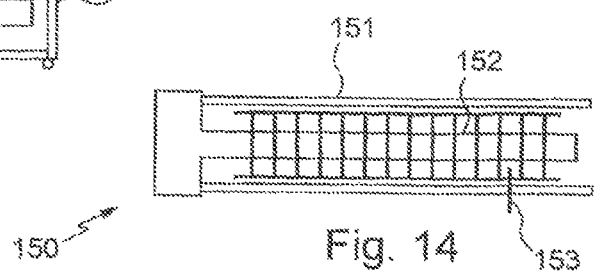
FIG. 14 is a view in cross section of another alternative form of a presentation device according to the invention.

Furthermore, the invention can be generalized to cases where the stick that might not necessarily have to be extracted from its confining enclosure; thus, FIG. 13 depicts a device 140 the confining enclosure 141 of which is provided, at the opposite end to the neck into which the head of the presentation stick is engaged, with a hole plugged by a removable lid 142; it is thus possible for the fragrance to be perceived simply by opening/closing the enclosure without having to extract the stick from this enclosure.

It is even possible (refer to the device 150 in FIG. 14) to plan for the enclosure 151 to be fitted with a mesh 152 interposed between the stick and the enclosure, and for movements of extracting or of retracting the mesh in relation to the enclosure, by acting on a peg 153 with which this mesh is fitted and which is accessible from the outside (visible bottom right in FIG. 14) to benefit the perception of the fragrance stored in the enclosure in question.

There are various possible ways of loading, in theory impregnating, a stick with a given fragrance.

Thus, one option is to schedule a daily, or some other frequency according to how much use is made of the devices, specific loading operation, for example by dipping the porous portion of the presentation stick under conditions, notably for a length of time, that cause the porous portion to become suitably laden with the fragrance in question through a capillary effect. It is a simple matter of calibration within the competence of those skilled in the art to define appropriate conditions for loading the stick with a given fragrance.

As an alternative, provision may be made for the stick to be impregnated at the time of its manufacture, which corresponds to fragrance presentation devices that have a limited life (although the life is still far greater than that of the strips of paper currently used).

Such an alternative may be of benefit for distributing samples to potential consumers to allow them to test them under various conditions during the course of the day.

Specifically, a presentation device according to the invention can be used in various ways:
- it can allow a selection to be made from a number of possible fragrances,
- it can be used for distributing samples allowing several tests under comfortable conditions,
- it can be used to capture fragrances for subsequent analysis thereof,
- etc.

It may be added that the test can be done by bringing the porous part into contact with the skin of a potential client, or simply by inhaling the perfume given off by the porous portion.

If desired, a seal connected to the holding head or to the neck may be provided between these two elements.

The invention claimed is:

1. A fragrance storing and releasing device designed to facilitate a person's choice of a fragrance to be worn by the person, said device comprising:
a confining enclosure having a closed lower end and an open upper end;
a presentation stick comprising:
a holding head designed for manipulation of the presentation stick, the holding head also designed to close the open upper end of the confining enclosure, the holding head being at least partially non-porous and is structured to prevent the fragrance from escaping from the confining enclosure in a resting configuration;
a stick part integrally formed with the holding head and designed to depend downwardly from the holding head within the confining enclosure;
a rigid porous portion integrally formed with the stick part, the porous portion designed to pass through the open upper end of the confining enclosure as the presentation stick is extracted from the confining enclosure for being presented to a fragrance-choosing person;
the presentation stick having an extracted configuration and at least one resting configuration;
in the extracted configuration at least the porous portion of the stick part of the presentation stick is withdrawn from the confining enclosure to allow the fragrance-choosing person to smell the fragrance;
in each of the at least one resting configuration the presentation stick is supported by the confining enclosure and the entirety of the porous portion of the stick part of the presentation stick is confined within the enclosure; and
in each of the at least one resting configuration a clearance is provided between an outer surface of the stick part and an inner surface of the confining enclosure.

2. The device of claim 1, wherein:
the porous portion extends to a free end of the presentation stick.

3. The device of claim 1, wherein:
in each of the at least one resting configuration the porous portion of the presentation stick is spaced from an inner bottom surface of the closed lower end of the confining enclosure.

4. The device of claim 1, wherein:
the confining enclosure comprises an internal cross sectional area that is no more than twice a cross-sectional area of the presentation stick.

5. The device of claim 1, wherein:
a cross section of the stick part below the holding head and a cross section of the confining enclosure below the holding head are substantially cylindrical.

6. A fragrance storing and releasing device designed to facilitate a person's choice of a fragrance to be worn by the person, said device comprising:
a confining enclosure having a closed lower end and an open upper end;
a presentation stick comprising:
a holding head designed for manipulation of the presentation stick, the holding head also designed to close the open upper end of the confining enclosure, the holding head being at least partially non-porous and preventing the fragrance from escaping from the confining enclosure in a resting configuration;
a stick part integrally formed with the holding head and designed to depend downwardly from the holding head within the confining enclosure;
a porous portion integrally formed with the stick part, the porous portion designed to pass through the open upper end of the confining enclosure as the presentation stick is extracted from the confining enclosure for being presented to a fragrance-choosing person;
the presentation stick having an extracted configuration and at least one resting configuration;
in the extracted configuration at least the porous portion of the stick part of the presentation stick is withdrawn from the confining enclosure to allow the fragrance-choosing person to smell the fragrance;
in each of the at least one resting configuration the presentation stick is supported by the confining enclosure and the entirety of the porous portion of the stick part of the presentation stick is confined within the enclosure;
in each of the at least one resting configuration a clearance is provided between an outer surface of the stick part and an inner surface of the confining enclosure; and a cross section of the stick part below the holding head and a cross section of the confining enclosure below the holding head being substantially cylindrical.

7. A fragrance storing and releasing device designed to facilitate a person's choice of a fragrance to be worn by the person, said device comprising:
   a confining enclosure having a closed lower end and an open upper end;
   a presentation stick comprising:
      a holding head designed for manipulation of the presentation stick, the holding head also designed to close the open upper end of the confining enclosure, the holding head being at least partially non-porous and preventing the fragrance from escaping from the confining enclosure in a resting configuration;
      a stick part integrally formed with the holding head and designed to depend downwardly from the holding head within the confining enclosure;
      a porous portion integrally formed with the stick part, the porous portion designed to pass through the open upper end of the confining enclosure as the presentation stick is extracted from the confining enclosure for being presented to a fragrance-choosing person;
   the presentation stick having an extracted configuration and at least one resting configuration;
   in the extracted configuration at least the porous portion of the stick part of the presentation stick is withdrawn from the confining enclosure to allow the fragrance-choosing person to smell the fragrance;
   in each of the at least one resting configuration the presentation stick is supported by the confining enclosure and the entirety of the porous portion of the stick part of the presentation stick is confined within the enclosure;
   in each of the at least one resting configuration a clearance is provided between an outer surface of the stick part and an inner surface of the confining enclosure;
   the confining enclosure extending longitudinally downwardly and comprises a cylindrical tube;
   a lower end of the cylindrical tube being the closed lower end of the confining enclosure and has a rounded longitudinal cross section; and
   the upper end of the cylindrical tube being the open upper end of the confining enclosure and has an outwardly flared neck.

8. A set of fragrance storing and releasing devices comprising:
   a plurality of fragrance storing and releasing devices, each of the plurality of fragrance storing and releasing devices designed to facilitate a person's choice of a fragrance to be worn by the person and comprising:
      a confining enclosure having a closed lower end and an open upper end;
      a presentation stick comprising:
         a holding head designed for manipulation of the presentation stick, the holding head also designed to close the open upper end of the confining enclosure;
         a stick part integrally formed with the holding head and designed to depend downwardly from the holding head within the confining enclosure;
         a porous portion integrally formed with the stick part, the porous portion designed to pass through the open upper end of the confining enclosure as the presentation stick is extracted from the confining enclosure for being presented to a fragrance-choosing person;
      the presentation stick having an extracted configuration and at least one resting configuration;
      in the extracted configuration at least the porous portion of the stick part of the presentation stick is withdrawn from the confining enclosure to allow the fragrance-choosing person to smell the fragrance;
      in each of the at least one resting configuration the presentation stick is supported by the confining enclosure and the entirety of the porous portion of the stick part of the presentation stick is confined within the enclosure; and
      in each of the at least one resting configuration a clearance is provided between an outer surface of the stick part and an inner surface of the confining enclosure;
   wherein said set further comprises:
      a single support;
      each confining enclosure of said plurality of fragrance storing and releasing devices are carried by said single support.

9. The set of devices of claim 8, wherein:
all of the plurality of storing and releasing devices have an identical geometry.

10. The set of devices of claim 8, further comprising:
presentation stick-marking elements designed to identify ones of the plurality of storing and releasing devices chosen by the fragrance-choosing person.

11. The set of devices of claim 10, wherein:
the marking elements are borne by respective ones of the holding heads of the chosen ones of the plurality of storing and releasing devices; and
the marking elements are oriented in respectively different ways according to positions of the presentation sticks in the confining enclosures.

12. The set of devices of claim 10, wherein:
the marking elements comprise rings designed to raise the holding heads of the plurality of holding and releasing devices in relation to the upper ends of respective ones of the confining enclosures of the holding and releasing devices in second resting configurations of respective ones of the presentation sticks.

13. The set of devices of claim 8, wherein:
the confining enclosures of the plurality of storing and releasing devices are arranged in an array.

14. The set of devices of claim 13, wherein:
the confining enclosures of the plurality of storing and releasing devices form rows and columns on the support.

15. The set of devices of claim 13, wherein:
the confining enclosures of the plurality of storing and releasing devices are staggered on the support.

16. The device of claim 1, wherein:
the stick part of the presentation stick below the holding head has a cross section that remains constant over an entirety of a length of the stick part.

17. The device of claim 1, wherein:
the stick part of the presentation stick below the holding head has a cross section that remains constant over an entirety of a length of the stick part except for a lower tip of the stick part, the lower tip being rounded in a longitudinal cross section of the stick part.

18. The device of claim 1, wherein:
a portion of the presentation stick below the holding head tapers toward a free end.

19. The device of claim 1, wherein:
the holding head is designed to plug the open end of the confining enclosure in a manner such that the presentation stick can be extracted from the confining enclosure and engaged therein by mere translation movement.

20. The device of claim 1, wherein:
the open upper end of the confining enclosure has a cross section designed to allow for the presentation stick to be introduced into the confining enclosure in either of at least two marking configurations;
in each of the two marking configurations, the presentation stick is in a respectively different rotational position in relation to the confining enclosure.

21. The device of claim 1, wherein:
the device consists of the presentation stick and the confining enclosure.

22. The device of claim 21, wherein:
the stick part of the presentation stick below the holding head has a cross section that remains constant over an entirety of a length of the stick part.

23. A fragrance storing and releasing device designed to facilitate a person's choice of a fragrance to be worn by the person, said device comprising:
a confining enclosure having a closed lower end and an open upper end;
a presentation stick comprising:
a holding head designed for manipulation of the presentation stick, the holding head also designed to close the open upper end of the confining enclosure, the holding head being at least partially non-porous and preventing the fragrance from escaping from the confining enclosure in a resting configuration;
a stick part integrally formed with the holding head and designed to depend downwardly from the holding head within the confining enclosure;
a porous portion integrally formed with the stick part, the porous portion designed to pass through the open upper end of the confining enclosure as the presentation stick is extracted from the confining enclosure for being presented to a fragrance-choosing person;
the presentation stick having an extracted configuration and at least one resting configuration;
in the extracted configuration at least the porous portion of the stick part of the presentation stick is withdrawn from the confining enclosure to allow the fragrance-choosing person to smell the fragrance;
in each of the at least one resting configuration the presentation stick is supported by the confining enclosure and the entirety of the porous portion of the stick part of the presentation stick is confined within the enclosure;
in each of the at least one resting configuration a clearance is provided between an outer surface of the stick part and an inner surface of the confining enclosure; and
the holding head, the stick part, and the porous portion being made as one piece.

24. The device of claim 23, wherein:
the one piece is one piece of porcelain.

25. The device of claim 1, wherein:
the clearance between the stick part and the confining enclosure ranges between approximately one millimeter and several millimeters.

26. The device of claim 1, wherein:
the holding head and the confining enclosure comprises means for lifting the holding head from the confining enclosure without a sliding of the holding head in relation to the confining enclosure.

27. The device of claim 1, wherein:
the porous portion of the presentation stick is an absorbent portion.

28. A method for storing and releasing fragrance using a plurality of devices, each of the plurality of devices according to claim 1, said method comprising:
loading the presentation stick of each of the plurality of devices with a respectively different fragrance;
placing each of the fragrance-loaded presentation sticks in the resting configuration within a respective confining enclosure in which the porous portion is positioned within the respective confining enclosure in a region of the enclosure where the fragrance exists only in a gaseous state;
extracting a series of presentation sticks from the respective confining enclosures in succession and presenting each of the sticks in succession to the fragrance-choosing person to allow the person to make a choice from among the different fragrances;
marking one or more of the presentation sticks laden with a chosen fragrance by fitting said one or more presentation stick back into respective confining enclosure(s) in one of the at least one resting configurations; and
extracting in succession at least some of the marked presentation sticks.

29. A fragrance storing and releasing device designed to facilitate a person's choice of a fragrance to be worn by the person, said device comprising:
a confining enclosure having a closed lower end and an open upper end;
the confining enclosure having a test tube shape comprising:
an at least substantially cylindrical tube portion between the closed lower end and the open upper end;
the tube portion having an uninterrupted continuous inner tubular surface between the closed lower end and the open upper end;
the open upper end is outwardly flared;
a presentation stick comprising:
a non-porous holding head designed for manipulation of the presentation stick, the holding head being designed to close the open upper end of the confining enclosure;
an at least substantially cylindrical stick part integrally formed with the holding head and designed to depend downwardly from the holding head within the tube portion of the confining enclosure;
a porous portion integrally formed with the stick part, the porous portion designed to pass through the open upper end of the confining enclosure as the presentation stick is extracted from the confining enclosure for being presented to a fragrance-choosing person;
the presentation stick having an extracted configuration and at least one resting configuration;
in each of the at least one resting configuration the presentation stick is supported by the confining enclosure and the entirety of the porous portion of the stick part of the presentation stick is confined within the enclosure; and
in each of the at least one resting configuration the inner tubular surface of the confining enclosure is spaced from an outer surface of the substantially cylindrical stick part.

30. The device of claim 29, wherein:
the confining enclosure is made of glass.

31. The device of claim 30, wherein:
the stick part of the presentation stick is made of glass or porcelain.

32. The device of claim 30, wherein:
the holding head and the stick part of the presentation stick are both made of glass or porcelain.

33. The device of claim 29, wherein:
the test tube shape further comprises a longitudinal cross section having a rounded lower end in longitudinal cross section.

34. The device of claim 29, wherein:
the device consists of said presentation stick and the confining enclosure.

35. The device of claim 29, wherein:
an entirety of a length of the stick part of the presentation stick below the holding head has a constant cross section.

* * * * *